July 29, 1975 O. L. WEEKS Plant Pat. 3,748
ROSE PLANT
Filed April 16, 1974
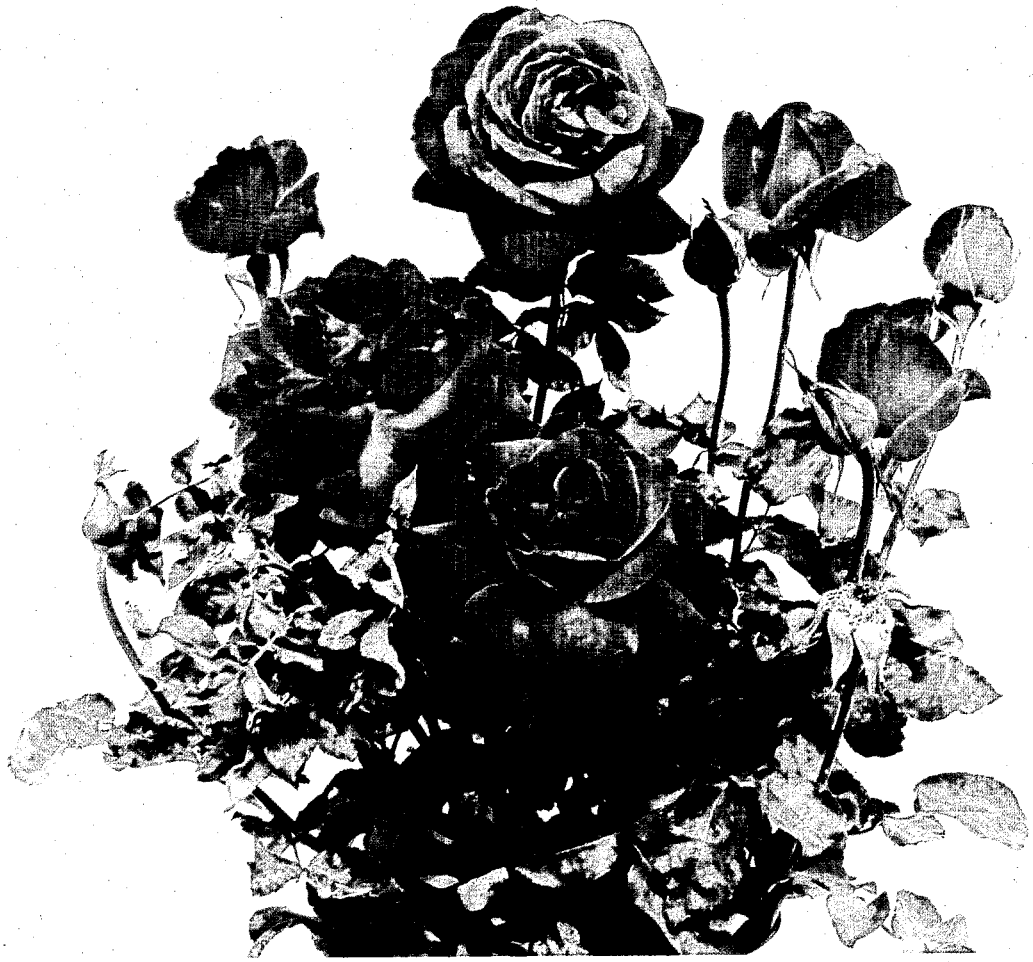

United States Patent

Plant Pat. 3,748

Patented July 29, 1975

3,748

ROSE PLANT

O. L. Weeks, 926 W. Philadelphia, Ontario, Calif. 91762

Filed Apr. 16, 1974, Ser. No. 461,403

Int .Cl. A01h 5/00

U.S. Cl. Plt.—20 1 Claim

The present invention relates to a new and distinct variety of rose plant of the hybrid grandiflora class, which was originated by me by crossing the rose variety known as "Jack O'Lantern" (Plant Pat. No. 1,985) with an unnamed and unpatented rose variety which is identified in my breeding records as #6040–A–10, the former being the seed parent and the latter being the pollen parent.

As the result of this breeding, I have produced a new and improved rose variety which is distinguished from its parents, as well as from all other rose varieties of which I am aware, as evidenced by the following unique combination of principal characteristics which are outstanding in the new variety:

(1) An ideally characteristic grandiflora type plant habit and growth;
(2) Abundant foliage of good quality which makes the plants attractive as garden plants during the growth cycle between blooming periods;
(3) A prolific blooming habit;
(4) A large flower size;
(5) An ability of the flowers to hold well on the plants for at least 5 or 6 days without fading or shattering; and
(6) A distinctive and attractive apple-red flower color which appears as a glowing and fluorescent-like overlay on the petals.

In comparison with its seed parent "Jack O'Lantern," my new variety is more vigorous, more compact and much more free blooming than this parent; its stems are much longer and although the flowers are borne in candelabra type clusters, the stems are long enough to cut and are more desirable for a good grandiflora rose than the shorter stems of the parent variety; and the flower color of the new variety is solid red, with no hint of other colors like the multi-colored blends of golds and oranges with tinges of red like the flowers of this parent.

As compared with its pollen parent, my new variety has a good grandiflora habit, with sufficient branching to make the plants attractive; it bears its flowers on strong candelabra stems which are long enough to cut, contrary to the more often shorter stems of the parent which are too short to cut; and the larger red flowers of my new variety have more luster and present a glowing or luminous effect contrary to the dull red flower color of this parent.

Asexual reproduction of my new rose variety by budding, as performed by me at Ontario, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significance are obvious:

Type: Hardy; tall; bush; outdoor; seedling; for cut flowers and for garden decoration.

Class: Hybrid grandiflora.

Breeding: Seedling.

*Seed parent.*—"Jack O'Lantern."

*Pollen parent.*—An unnamed seedling.

Propagation: Holds its distinguishing characteristics through succeeding propagations by budding.

FLOWERS

Locality where grown and observed: Ontario, Calif.

Flowers borne: Singly and 2 or 3 to stem; in irregular clusters; on short to medium long stems of normal strength.

Quantity of bloom: Free and abundant, both outdoors and in greenhouse.

Continuity: From intermittent to continuous.

Fragrance: Slight.

Bud:

*Peduncle.*—From short to medium length; medium caliper; erect; entirely smooth. Color—From light to medium green.

*Before calyx breaks.*—Size—Small. Form—From short to medium length; oval; with a conspicuous neck; with foliaceous appendages on the surface of the bud; with slender bristle-like foliaceous parts extending beyond the tip of the bud equal to ½ to ¾ or more of its length.

*As calyx breaks.*—Color—Red, between Medium Red, 40–11 and a darker and fuller Red, 40–12.

*As petals first open.*—Size—Small. Form—Short; mostly orbicular. Color (outside)—Between Medium Red, 40–11 and Darker Red, 40–12, with a medium segment of Deep Yellow, 26–8 to deeper 26–9.

*Opening.*—Opens up well.

Bloom:

*Size (when fully open).*—Large; from 4 inches to 5 inches.

*Petalage.*—Very double, but stamens not hidden; from 48 to 52 petals; arranged regularly.

*Form.*—Somewhat open, high-centered and globular at first and becoming open, high-centered and globular; petals at first being tightly rolled outward, but later becoming loosely cupped and rolled outward at maturity.

Petals:

*Texture.*—Fairly thick; soft.

*Appearance.*—Inside—Velvety. Outside—Velvety.

*Shape.*—Outside—Orbicular; somewhat scalloped; with apex flat and with 1 notch. Intermediate—Somewhat orbicular; somewhat scalloped; with apex flat and with none or 1 notch. Inside—Somewhat orbicular; irregularly scalloped; with apex flat and with none or 1 notch.

This description of a newly opened flower was made from a rose grown outdoors in the month of October at Ontario, Calif.:

*Color.*—Outer petal—Outside surface—Between Medium Red, 40–11 and slightly lighter Red, 40–10, with a medium size basal segment of Greenish Yellow, between 25–7 and 25–8. Inside surface—A blend of essentially the same Reds, 40–10, 40–11 and 40–12, with a small basal segment of Greenish Yellow, between 20–5, 20–7 and 20–8. Intermediate petal—Outside surface—Between Medium Red, 40–10 and a more Cherry Red, 39–10, with a basal segment of Yellowish Green, between 25–8 and 25–9. Inside surface—Between Cherry Red, 39–10 and 39–11, with a basal segment of Greenish Yellow, between 25–8 and 25–9. Inner petal—Outside surface—Between Medium Red, 40–10 and 40–11, with a basal segment of Yellowish Green, between 25–8 and 25–9. Inside surface—Blend of Cherry Red, 39–10, 39–11 and 39–12, with a basal segment of Yellowish Green, between 25–8 and 25–9.

This description was made from a rose that was open for three days outdoors during the month of October, at Ontario, Calif.:

*Color.*—Outer petal—Outside surface — Between Cherry Red, 39–8 and 39–9 and Medium Red, 40–9, with a basal segment of Yellowish Green, between 26–8 and 26–9. Inside surface—Blend upward of Medium Red, between 40–9 and 40–11, with a basal segment of Yellowish Green, between 25–8 and 26–8. Inner petal—Outside surface—Orange-tinted Cherry Red, between 38–8 and 38–9, with a basal segment of Yellowish Green, between 25–9 and 25–8. Inside surface—Cherry Red, between 39–8 and 39–9, with a basal segment of Yellowish Green, between 25–8 and 26–8.

*General color effect.*—Newly opened flower—Blend of Medium Red, between 40–10 and 40–11. 3-days open—Blend of Cherry Reds, between 39–8, 39–9 and 39–10.

*Behavior*—Drop off fairly cleanly.

*Flower longevity.*—On bush in garden—5 or 6 days in October. Cut roses grown outdoors and kept at living room temperature—3 days in October.

REPRODUCTIVE ORGANS

Stamens: From very few to medium number; arranged irregularly; tucked in calyx.

Filaments: From medium length to long; few with anthers. Color—Yellowish.

Anthers: Very small; open at various times. Color—Brown.

Pollen: Moderate abundance. Color—lemon gold.

Pistils: From few to medium number.

Styles: Uneven; from short to medium length; medium caliper; somewhat bunched.

Stigma: Color—Yellowish red.

Ovaries: All enclosed in calyx.

Hips: None observed.

Sepals: Permanent; moderately long; spear-shaped; recurved. Color—Light green, with some brown on outside.

Seeds: None observed.

PLANT

Foliage:

*Leaves.*—Compound of 3–5–7 leaflets; normal abundance; medium size; moderately heavy; somewhat leathery and glossy.

*Leaflets.*—Shape—Ovate. Apex — Acute. Base—Fairly round. Margin—Serrate.

*Color.*—Mature—Upper surface—Moderately dark green. Under surface—Moderately green, with some bronze red. Young—Upper surface—Moderately bronze and red, with some green overtones. Under surface—Moderately dark bronzey red.

*Rachis (the supporting stem of the compound leaf).*—Light weight. Upper side —Smooth. Under side—Generally smooth, but mildly prickly.

*Stipules.*—Medium length; medium width; with moderately long points turning out at an angle of more than 45°; recurved toward the stem.

Disease and insect resistance: No evidence of blackspot; average resistance to powdery mildew during regular growing season, so appearance of mildew in the drawing is a typical and above average resistance to red spider, as determined by comparison with other rose varieties grown under the same conditions at Ontario, Calif.

Growth:

*Habit.*—Tall; upright; much branched.

*Growth.*—Free; vigorous.

*Canes.*—Moderately heavy caliper.

*Main stem.*—Color—Dull green. Large prickles—From few to several; medium long; straight; with fairly short, oval base. Color—Brown. Small prickles—Few. Color—Brown. Hairs—From none to few.

*Branches.*—Color—Dull green. Large prickles—From none to few; medium long; some straight and some hooked downward; with short, oval base. Color—Brown. Small prickles—From none to few. Color—Reddish at base. Hairs—Few. Color—Grey-green.

*New shoots.*—Color—From green to reddish. Large prickles—Few; medium long; straight; with narrow, oval base. Color—Reddish. Small prickles—From none to few. Color—From reddish to green. Hairs—From none to few. Color—Reddish.

I claim:

1. A new and distinct variety of rose plant of the hybrid grandiflora class, substantially as herein shown and described, characterized particularly as to novelty by the unique combination of an ideally characteristic grandiflora type plant habit and growth, abundant foliage of good quality which makes the plants attractive as garden plants during the growth cycle between blooming periods, a prolific blooming habit, a large flower size, an ability of the flowers to hold well on the plants for at least 5 or 6 days without fading or shattering, and a distinctive and attractive apple-red flower color which appears as a glowing and fluorescent-like overlay on the petals.

No references cited.

ROBERT E. BAGWILL, Primary Examiner